US00PP11927P2

(12) United States Plant Patent
Craig et al.

(10) Patent No.: US PP11,927 P2
(45) Date of Patent: Jun. 12, 2001

(54) REGAL PELARGONIUM PLANT NAMED 'SYMPHONY'

(75) Inventors: Richard Craig, State College, PA (US); Soumaila Sanogo, Ames, IA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/336,453

(22) Filed: Jun. 18, 1999

(51) Int. Cl.[7] ..... A01H 5/00

(52) U.S. Cl. ..... Plt./331

(58) Field of Search ..... Plt./331, 324

*Primary Examiner*—Bruce R. Campell
*Assistant Examiner*—Kent L. Bell
(74) *Attorney, Agent, or Firm*—Webb Ziesenheim Logsdon Orkin & Hanson, P.C.

(57) ABSTRACT

A new and distinct regal Pelargonium with medium pink blooms with an eye and veining ranging from deep burgundy to candy pink accented by medium green foliage. The new cultivar has improved plant habit, cutting production, rooting speed, and flowering speed over 'Josy'.

2 Drawing Sheets

BACKGROUND OF THE INVENTION

This discovery relates to a new and distinct cultivar of regal Pelargonium (*Pelargonium×domesticum*) identified by the name of 'Symphony', Breeder No. 93-35-1 and Oglevee, Ltd. No. 29. The cultivar was discovered in an organized, scientifically design breeding program conducted at the Department of Horticulture, The Pennsylvania State University, University Park, Penna. The new cultivar is the offspring of two unpatented breeding cultivars, Breeder Nos. 90-139-7 (female) and 90-49-2 (male). The new cultivar is less compact than tht seed parent and the number of inflorescences are similar to both parents. The purpose of the breeding program was to create new regal Pelargonium genotypes with clear, bright flower colors, excellent propagation characteristics, compact growth habit, predictable and consistent flowering response and good postharvest quality. The new cultivar was produced from prior selections developed at The Pennsylvania State University since 1977. The pedigree of this cultivar includes the patented cultivars 'Allure' and 'Fantasy' (U.S. Plant Pat. No. 7,467 and 7,538, respectively) and other unpatented cultivars as shown in FIG. 2.

The new cultivar was first asexually propagated by cuttings at The Pennsylvania State University and subsequently at Oglevee, Ltd., 152 Oglevee Lane, Connellsville, Penna. The new cultivar reproduces true and has been found to retain its distinct charcteristics through successive propagation.

The new cultivar, when grown in a glass greenhouse in Connellsville, Penna using full light, 60° F. night temperature, 68° F.day temperature and grown in a soilless media with constant fertilizer at 150–200 ppm nitrogen and potassium, has a response time from a rooted cutting to a flowering plant in a 6 inch pot of fourteen weeks. Rooted cuttings potted Oct. 15, 1997 flowered on Feb. 9, 1998.

DESCRIPTION OF THE DRAWINGS

FIG. 1 depicts a top perspective view of the new cultivar.

Figure 2:
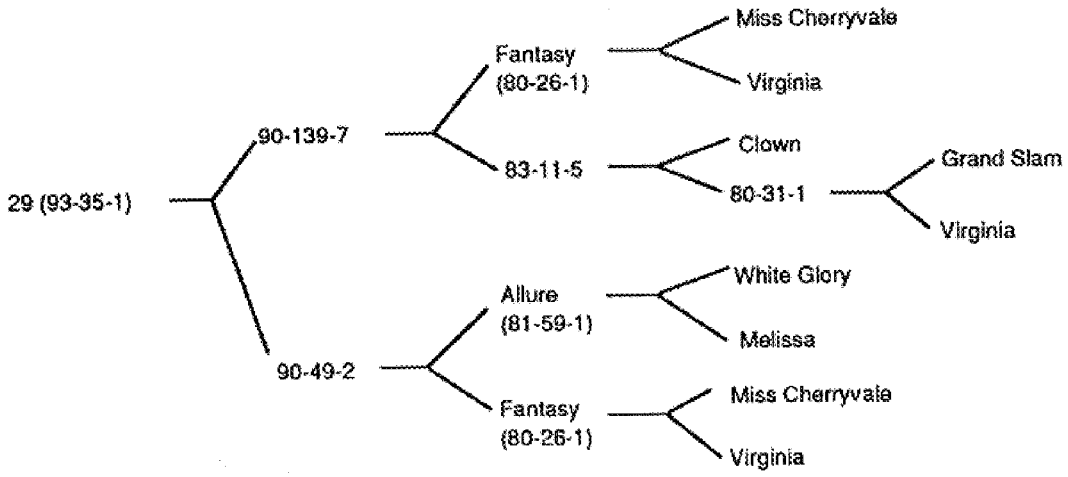
FIG. 2 depicts a flowchart of the pedigree of the new cultivar.

Colors depicted in FIG. 1 are as nearly true as is possible with a color illustration of this type.

DESCRIPTION OF THE PLANT

The following detailed descriptions set forth the characteristics of the new cultivar. The data which define these characteristics were collected from asexual reproductions carried out in Connellsville, Penna. The color readings on a plant grown in a 5 inch pot were taken indoors under 200–220 foot candles of cool white fluorescent light. Color references are primarily to The R.H.S. Colour Chart of The Royal Horticultural Society of London. The data was taken from plants 14 weeks old.

THE PLANT

Classification:
- *Botanical.*—*Pelargonium×domesticum.*
- *Varietal.*—Regal Pelargonium named 'Symphony'.

Form: Medium mound.

Height: 29.0–32.0 cm from soil line to the top of the foliage, 36.0–40.0 cm from the soil line to the top of the umbels.

Growth: Medium plant habit with free basal brancing; continuous flowering.

Strength: No artificial support needed.

Foliage: Stalked leaf attachement.

Leaves:
- *Size.*—7.8–9.0 cm across.
- *Shape.*—Reniform, truncate base; 5.0–6.0 cm in length with rounded leaf apex.
- *Margin.*—Serratedy.
- *Texture.*—Pubescent, somewhat leathery.
- *Color.*—Top: Green Group 137B. Bottom: Green Group 138B. Zone: None.
- *Ribs and veins.*—Venation; Palmate. Color: Green Group 139D for upper surface.

Petioles:
- *Length.*—6.0–6.5 cm.
- *Color.*—Yellow-Green Group 146C.

Stem:
- *Color.*—Yellow-Green Group 146C.
- *Length.*—5.5–7.5 cm.
- *Internode length.*—2.75–3.0 cm.
- *Roots.*—Time to develop: 14–21 days. Description: Fibrous.

THE BUD

Shape: Elliptical cluster; individual bud is elliptical.
Size of umbel: 2.5–3.5 cm across; individual bud length 2.0 cm and width 0.5–0.7 cm.
Color: Yellow-Green Group 144A.

INFLORESCENCE

Blooming habit: Large flowers formign a full, continuous flower head.
Borne: Umbel, Flowers on pedicel, pedicel on peduncle.
Flowers:
*Number of flowers per umbel.*—4–8.
*Umbel depth.*—3.0–4.5 cm.
*Flower depth.*—2.0–3.0 cm.
Open flowers:
*Form.*—Ruffled, cupped.
*Size of fully open bloom.*—Umbels: 10.0–12.0 cm across.
*Color.*—Top: Upper two petals are white at base. Dark eye of Greyed-Purple Group 187A fading to Red-Purple Group 58B and then to Red-Purple Group 62C at the edge. Dark veining ranging from Greyed-Purple Group 187B to Red-Purple Group 58B. Bottom: Upper two petals have pale pink edge of Red-Purple Group 62D with dark color from the eye showing through ranging from Greyed-Purple Group 187C to Red-Purple Group 58D. Lower three to four petals are white to pale pink with eye showing through. Eye: Eye is Greyed-Purple 187A at darkest to Red-Purple Group 58D being the lightest. Lower three to four petals have a less significant eye of the same colors with a more visible background color of Red-Purple Group 62A.
*Petals.*—Number: Some flowers have 5 (2 upper and 3 lower). Other flowers have 6 (2 upper and 4 lower). Size: 1.5–2.0 cm wide; 1.5–1.8 cm long. Overall shape: Elliptical. Apex shape: Obovate. Base shape: Acute. Texture and appearance: Stainy, ruffled, reflective; appears from a distance as pale pink on lower petals with top half of bloom having a large deep burgundy eye with colors fading to a crisp candy pink and pale pink.
Petaloids: None.
Sepal:
*Size.*—1.5 cm long; 0.5–1.0 cm wide.
*Apex shape.*—Acuminate.
*Base shape.*—Round.
*Color.*—Yellow-Green Group 144A.
Pedicel:
*Length.*—2.0 cm.
*Color.*—Yellow-Green Group 146C.
Peduncle:
*Length.*—6.5–8.0 cm.
*Color.*—Yellow-Green Group 146C.
*Natural flowering season.*—Spring.
Disease resistance: None observed.
Lasting quality: Flowers will hold and continue to open for 14 to 21 days in the home environment.

REPRODUCTIVE ORGANS

Stamens:
*Anthers.*—3.0–4.0 mm long.
*Filaments.*—Length: 1.2–1.5 cm. Color: White.
*Pollen color.*—Golden orange.
*Pollen.*—Plentiful.
Pistil:
*Number.*—1; five parted.
*Length.*—1.8 cm.
*Stigma color.*—Red-Purple Group 59A.
*Style.*—1.3 cm long.
*Ovaries.*—Light green; pubescent; superior; 8.0–9.0 mm long.
Fruit: None observed.

GENERAL CHARACTERISTICS

'Symphony' is similar in color to the variety 'Josy' U.S. Plant Pat. No. 6,019. Plant habit, cutting production, rooting speed, and flowering speed are all improved over 'Josy'.

We claim:

1. A new and distinct cultivar of regal Pelargonium plant named 'Symphony' substantially as described and iillustrated herein.

* * * * *

UNITED STATES PATENT AND TRADEMARK OFFICE

CERTIFICATE OF CORRECTION

PATENT NO. : PP 11,927 E
DATED : June 12, 2001
INVENTOR(S) : Richard Craig et al.

It is certified that error appears in the above-identified patent and that said Letters Patent is hereby corrected as shown below:

Column 1,
Line 11, "tht seed" should read -- the seed --.
Line 32, "68° F.day" should read -- 68° F. day --.

Column 2,
Line 21, "basal brancing" should read -- basal branching --.
Line 29, "*Margin.* --Serratedy." should read -- *Margin.*--Serrated--.

Column 3,
Line 10, "Blooming habit: Large Flowers formign" should read -- Blooming habit: Large flowers forming --.
Under *Petals*, line 5, "Stainy" should read -- Satiny --.

Column 4, Claim 1,
Lines 2-3, "iillustrated" should read -- illustrated --.

Signed and Sealed this

Eighteenth Day of December, 2001

*Attest:*

*Attesting Officer*

JAMES E. ROGAN
*Director of the United States Patent and Trademark Office*

UNITED STATES PATENT AND TRADEMARK OFFICE

CERTIFICATE OF CORRECTION

PATENT NO. : PP 11,927 P2
APPLICATION NO. : 09/336453
DATED : June 12, 2001
INVENTOR(S) : Craig et al.

It is certified that error appears in the above-identified patent and that said Letters Patent is hereby corrected as shown below:

Title Pg, Col. 1, Line 1, Insert:

-- STATEMENT REGARDING FEDERALLY SPONSORED RESEARCH
This invention was made with government support under
Hatch Act Project Nos. PEN03030 and PEN03393, awarded by the USDA.
The Government has certain rights in the invention. --

Signed and Sealed this

Twelfth Day of August, 2008

JON W. DUDAS
*Director of the United States Patent and Trademark Office*